United States Patent [19]

Mueller et al.

[11] Patent Number: 4,469,885

[45] Date of Patent: Sep. 4, 1984

[54] HALOGENATED PROTEASE INHIBITORS

[75] Inventors: Richard A. Mueller, Glencoe; Richard A. Partis, Evanston, both of Ill.

[73] Assignee: G. D. Searle & Co., Skokie, Ill.

[21] Appl. No.: 492,843

[22] Filed: May 9, 1983

[51] Int. Cl.³ .............................................. C07C 65/32
[52] U.S. Cl. ................... 562/459; 548/239; 424/308; 560/51; 560/65; 560/103; 560/104; 562/474; 562/493
[58] Field of Search ........................ 560/51, 65, 104; 562/459, 474, 493

[56] References Cited

U.S. PATENT DOCUMENTS 3,988,471 10/1976 Kohn ................................... 424/301
4,276,431 6/1981 Schnegg et al. ...................... 560/67

FOREIGN PATENT DOCUMENTS

EP-9699 4/1980 European Pat. Off. .............. 560/64
44-27216 11/1969 Japan ................................... 562/475

OTHER PUBLICATIONS

Moffett, R. Bibal, J. of Med. & Pharm. Chem., vol. 2, #2, 1960, pp. 213-227.

Primary Examiner—Paul J. Killos
Attorney, Agent, or Firm—John J. McDonnell

[57] ABSTRACT

This invention relates to novel compounds for preventing or retarding the degradation of elastin or other proteins and therefore preventing or retarding the disease states caused by said degradation, of the formula:

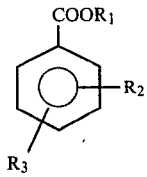

or its pharmacologically acceptable salts. The invention also relates to novel methods and intermediates for making the compounds.

11 Claims, No Drawings

HALOGENATED PROTEASE INHIBITORS

BACKGROUND OF THE INVENTION (a) Field of the Invention

This invention, in its broadest aspect, relates to enzyme inhibitors. In particular, it relates to compounds of Formula I which are useful in preventing or treating disease states caused by the action of proteases and other enzymes on mammalian elastin or other proteins. More particularly, the invention relates to certain novel compounds useful in preventing or treating disease states caused by the degradative action of elastases or cathepsin G. In another aspect, it relates to novel intermediates of Formula II for preparing compounds of Formula I.

Elastin is the functional protein component of elastic fiber tissues, a component of connective tissues. Elastic tissue is relatively rich in elastin and has a distinct rubber-like property. Most specifically, the ligamentum nuchae and the vocal cords, the vertebral ligamenta flava, the aorta, and the pulmonary arteries of some mammals are considered elastic tissues. Elastic cartilaginous tissues such as those present in the ear and epiglottis are a specialized form of elastic tissue. Lung, bronchi and skin also contain elastin and are considered elastic tissue. Sandberg, et al., *New England Journal of Medicine*, Mar. 5, 1981, 566–579.

Elastase is an elastinolytic enzyme which causes degradation and fragmentation of elastic fibers by its catalytic activity against elastin. Elastases originate from a number of sources and can be found in microorganisms, snake venoms and a number of mammalian cells and tissues including pancreas, polymorphonuclear leukocytes, and macrophages. In a normally functioning mammal, elastase is required for turnover of damaged cells and the digestion of certain invading bacteria. This invention in particular relates to the class of elastases known as the Serine Proteases.

Excessive elastin degradation has been associated with pulmonary emphysema, adult respiratory-distress syndrome, arthritis, atherosclerosis, certain skin diseases, and certain inflammatory processes leading to localized protein breakdown. Werb, et al., *Journal of Investigative Dermatology*, 79: 154S–159S, (1982); Rinaldo, et al., *New England Journal of Medicine*, 306: 900–909, (1982). By inhibiting elastase therefore it is possible to mediate, eliminate or treat a wide variey of disease conditions.

A number of inhibitors of elastase are known. Peptide chloromethyl ketones have been shown to be irreversible inhibitors of elastase. But difficulties must be considered when the in vivo use of peptide chloromethyl ketones is contemplated. The compounds are electrophiles and can react with good nucleophiles such as the thiol groups of glutathione and various proteins. During any long term treatment with these inhibitors, such non-specific alkylation could lead to the introduction of new antigenetic determinants and an autoimmune response and/or could behave similarly to the known nitrogen mustards, etc. Peptides containing aza-amino acid residues (aza peptides) are another class of inhibitors. The effectiveness of aza-peptides as elastase inhibitors depends on the rate of acylation, which in most cases is instantaneous, and also on the rate of deacylation. As such, these compounds while useful tools in studying the in vitro properties of elastase are still largely unsuitable for in vivo use.

(b) Information Disclosure

The treatment of certain disease states by inhibitors of elastase is known as described above.

SUMMARY OF THE INVENTION

This invention relates to novel compounds for preventing or retarding the degradation of elastin and other proteins in mammals, of the formula:

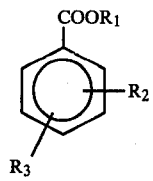

wherein $R_1$ is:
  (a) hydrogen; or
  (b) alkyl of 1 to 6 carbon atoms, inclusive;
wherein $R_2$ is:
  (a) halogen;
  (b) trifluoromethyl
wherein $R_3$ is:
  (a) —C(O)$R_4$;
  (b) —CH(OH)$R_4$;
  (c) —CH$_2$$R_4$; or
  (d) —CH=CH$R_4$;
wherein $R_4$ is alkyl of 13 to 25 carbon atoms inclusive and the pharmacologically acceptable base addition salts thereof.

In addition, the invention relates to novel intermediates useful in the preparation of the halogen compounds of the invention of the formula:

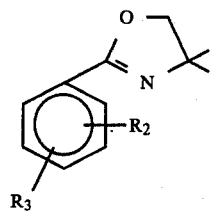

wherein $R_2$ and $R_3$ are as described above.

Examples of alkyl of 1 to 6 carbon atoms inclusive are methyl, ethyl, propyl, butyl, pentyl, hexyl and the isomeric forms thereof.

Examples of halogen are chlorine, fluorine and bromine.

Examples of alkyl of 13 to 25 carbon atoms inclusive are dodecanes, dodecenes, hexadecanes, hexadecenes, pentadecanes, pentadecenes, eicosadecanes, eicosadecenes and the like, as well as their branched chain isomers.

Salts of compounds of Formula I wherein, $R_1$=H can be prepared for example by neutralization with the appropriate amount of an inorganic or organic base such as sodium hydroxide, potassium hydroxide, calcium hydroxide, magnesium hydroxide, ammonia, trialkylamine, dialkylamine, monoalkylamine, dibasic amino acids, sodium acetate, potassium benzoate, triethanolamine and like bases.

The compounds of the invention are all inhibitors of leucocyte elastase and cathepsin G. Since elastase is involved in the breakdown of elastin and subsequently involved in a number of disease states, a compound which blocks the action of elastase will be useful in the management, treatment and prevention of such diseases. Elastase, in addition to degrading elastin, also will hydrolyse methoxysuccinyl-ala-ala-pro-val-nitroanalide (MSN), a highly selective synthetic substance. Nakajima, K., et al., *J. Biol. Chem.* 254, 4027 (1979) This is useful in measuring inhibition of elastase because the hydrolysis of MSN is easily quantitated by measuring the release of p-nitroaniline spectrophotometrically. Therefore, the degree of elastase inhibition can be readily measured by noting the rate of inhibition of the hydrolysis of MSN. The compounds of the invention are therefore tested in vitro as follows. The rate of hydrolysis of methoxysuccinyl-ala-ala-pro-val-nitroanalide by human leukocyte elastase is monitored spectrophotometrically in the presence and absence of test compound. The inhibition of the enzymatic reaction by 20% or more is taken as positive inhibition. $IC_{50}$ values are then determined.

The following procedure can be used to test the compounds in vivo (collagen-induced rat arthritis model). Inbred female Wistar rats (200–230 G) are randomly assigned to 3 groups of 30 animals each. Arthritis is induced by intradermal injection of bovine nasal septum type II collagen in incomplete Freunds adjuvant.

Drug treatment is oral, once daily in 0.5 ml carboxymethyl cellulose from day 0 until sacrifice:

Group 1: Test compound 50–100 mg/kg/day
Group 2: Phenylbutazone 40 mg/kg/day (positive control)
Group 3: 1%V/V carboxymethyl cellulose (negative control)

(1) Physical measurements of hind paws are made for (a) swelling across plantar region (b) malleolar thickening (c) extensibility of ankle joint. Results are subject to systematic statistical evaluation.

(2) Histological examination of hind paws are made in groups of 5 animals sacrificed at days, 7, 14, 21 and 23. Sections are taken at 3 levels through each foot and examined for indications of disease progression.

The method is based on that of Trentham, D. B. Townes, A. S. and Kang, A. H. in J. Exp. Med. 146, 357–968, (1977) and results are evaluated thereby.

During periods of active rheumatoid arthritis, vast numbers of human neutrophils are attracted to diseased joints where they engage in phagocytosis of locally generated immune complexes and tissue debris. During the process, enzymes (primarily elastase and cathepsin G) are released into the joint spaces. Elastase has the capacity in this situation to degrade synovial cartilage and collagen and contribute to joint destruction in a synergistic process with cathepsin G. Cathepsin G also causes conversion of angiotensin I to angiotensin II, Reilley, C. F., et al., *J. Biol. Chem.*, 257, 8619 (1982) and angiotensinogen to angiotensin II, which is associated with inflammatory processes. Tonnesen, M. G., et al., *J. Clin. Invest.*, 69, 25 (1982). Natural elastase inhibitors (macro molecules such as $\alpha_1$-proteinase inhibitor) already exist in normal serum and synovial fluid and may prevent precipitous joint destruction. Oxidation of the natural inhibitor (to the sulfoxide form) renders this material inactive. Wong, P. S. and J. Travis, *Biochem Biophys. Res. Commun.*, 96, 1449 (1980). Exogenous smaller molecular weight inhibitors of the invention can gain access to the micro-environments within the joint space not accessible to the natural inhibitors due to their molecular size, oxidation, charge repulsion or lipid solubility, and thereby inhibit or prevent further elastase-related destruction. In addition, pulmonary emphysema is a disease characterized by a progressive uninhibited proteolysis of lung tissue by enzymes such as elastase which in this case are released from leukocytes. People who are homozygotes in an $\alpha_1$-antitrypsin deficiency are predisposed to the disease. See, e.g., Turimo, et al., *Amer. J. Med.*, Vol 57, pp. 493–503 (1974). The compounds of the invention could also be used to prevent the further proteolysis of lung tissue. Again, the ability of the compounds to inhibit cathepsin G is desirable, since the combination of elastase and cathepsin G has been reported to be five times as efficient at degrading elastin as is elastase alone. Boudier, C., et al., *J. Biol. Chem.* 256, 10256 (1981). In a like manner, adult respiratory-distress syndrome, certain skin diseases, ageing, and certain inflammatory processes where the disease state is connected with the localized breakdown of protein by elastase could be treated by elastase inhibitors, such as the compounds of this invention. For example, degradation of fibronectin, an important biological substance, could be inhibited. McDonald, J. A., and D. G. Kelley, *J. Biol. Chem.*, 255, 8848 (1980). The compounds may also be useful in the treatment of other enzyme related diseases, such as fibrosis related to prolylhydroxylase, hypercholesterolemia related to HMG CoA reductase, and the like. This invention is not limited to these examples. One skilled in the art could readily use the compounds of the invention for other protease or elastase related diseases or conditions.

The compounds can be administered in a number of dosage forms. A preferred method of delivery would be in such a manner so as to localize the action of the inhibitor. So, for example, in arthritis, the compounds could be injected directly into the affected joint, or for emphysema, the compounds could be inhaled using an aerosol or other appropriate spray. In any event, the compounds may be administered in any conventional manner. The compounds could be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory skin diseases, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for elastase inhibition by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The compounds of this invention are prepared by the general methods illustrated in Charts A through C. Chart A: Substituted 4- or 5-halobenzoic acids of Formula XI are converted to oxazoline derivatives of Formula XII by conversion of the acids to corresponding acyl halides, followed next by reaction with an appropriate ethanolamine and then by ring closure of the resultant intermediate amides. Preferred conditions for forming acyl halides include reaction of Formula XI, where X is bromine, with thionyl halides, such as thionyl chloride or thionyl bromide, in an unreactive solvent, such as carbon tetrachloride. Preferred conditions for amide formation include reaction of the acyl halides with 2-amino-2-methylpropanol in an unreactive organic solvent, such as dichloromethane. Preferred conditions for ring closure include reaction of the amide intermediates with thionyl chloride either neat or in an unreactive organic solvent, such as diethyl ether; the resultant hydrochloride salts are neutralized for further reactions by methods known to those skilled in the art.

Intermediate halophenyloxazolines, Formula XII, are activated for subsequent reaction by metallation procedures, which can form, for example, lithio or Grignard intermediates of Formula XIII. Lithiated intermediates ($M=Li^+$) may be formed by reaction of Formula XII with an alkyllithium or aryllithium in inert solvent at temperatures below about $-60°$. Preferred conditions include reaction with n-butyllithium in tetrahydrofuran at $-70°$ under a dry argon atmosphere. Subsequent reactions, as described below, are performed in situ at $-50°$ to $-70°$. Grignard intermediates ($M=MgX^+$) may be formed by reaction of Formula XII with magnesium metal in inert solvent. Preferred conditions include reaction with magnesium in tetrahydrofuran under a dry argon atmosphere. Subsequent reactions, as described below, are performed in situ at about $0°$. Metallated intermediates of Formula XIII ($M=Li^+$ or $MgX^+$) may thus react with aldehydes to form alcohol derivates of Formula XIV. For lithiated intermediates, preferred conditions include adding solutions of appropriate aldehydes, such as octadecanal, in precooled tetrahydrofuran (below $0°$) to the colder lithium reagent solutions (see above), followed, after the reaction is complete, by a water quench. For Grignard intermediates, preferred conditions include adding appropriate aldehydes directly to the cold Grignard solutions (see above), followed by reaction at room temperature and a water quench. Compounds of Formula XIV thus formed may be purified, after aqueous workup, by extraction into organic solvents, such as ethyl acetate, diethyl ether, or dichloromethane, and subsequent column chromatography on silica gel. Metallated intermediates of Formula XIII ($M=Li^+$ or $MgX^+$) may also react with acyl halides to form ketone derivates of Formula XV, using methods similar to those used in the above reactions with aldehydes. Preferred acyl halides include alkanoyl chlorides, such as octadecanoyl chloride.

Compounds of Formulas XIV and XV may be interconverted by methods known to those skilled in the art. For example, ketones of Formula XV may be converted to the corresponding alcohols, Formula XIV, by reaction with activated hydride reducing agents. Preferred conditions include reaction with sodium borohydride in ethanol. Alcohols of Formula XIV may also be converted back to ketones, Formula XV, by reaction with suitable oxidizing agents. Preferred conditions include reaction with a suspension of manganese dioxide in an unreactive organic solvent, such as dichloromethane.

Oxazolines of Formulas XIV (alcohols) and XV (ketones) may each be converted to respective corresponding benzoic acids, Formula XVI by acid hydrolysis. Preferred conditions include heating at $70°-90°$ in ca. 4.5N hydrochloric acid for about four days. Those compounds which crystallize upon standing may be purified by recrystallization using, for example, methanol or methanol/diethyl ether. Those compounds which do not crystallize may be purified by extraction into an organic solvent, such as dichloromethane or ethyl acetate, followed by column chromatography on silica gel. Chart B: Alcohols of Formula XXI (i.e., Formula XVI of Chart A, where $X=OH$, $Y=H$) can be converted to other compounds of this invention. For example, alcohols of Formula XXI may be dehydrated by heating in the presence of an acid catalyst, giving alkenes of Formula XXII. Preferred conditions include heating at reflux in benzene or toluene containing p-toluenesulfonic acid. Alkenes of Formula XXII may be reduced to corresponding alkanes, Formula XXIII. Preferred conditions include hydrogenation in an organic solvent, such as acetic acid, over a noble metal catalyst, such as palladium, rhodium, or Raney nickel.

Carboxylic acids and esters prepared by the methods described in this invention may be interconverted by methods known to those skilled in the art. For example, carboxylic acids of Formula XXIV can be converted to corresponding esters, Formula XXV. Preferred methods includes heating an acidified solution of Formula XXIV in the appropriate alkyl alcohol or reaction of Formula XXIV with a diazoalkane, such as diazomethane. Esters of Formula XXV can in turn be hydrolyzed to free acids, Formula XXIV. Preferred conditions include alkali metal hydroxides in water, followed by neutralization with dilute mineral acid. Corresponding carboxylic acid salts (having a metal or other positively charged counter ion) may readily be prepared by methods known to those skilled in the art. Chart C: An alternative method for preparing compounds of this invention employs substituted toluenes, Formula XXXI. For example, compounds of Formula XXXI undergo Friedel-Crafts acylation with acyl halides in the presence of Lewis acids, giving compounds of Formula XXXII. Preferred conditions include reaction with an alkanoyl chloride, such as octadecanoyl chloride, in refluxing carbon disulfide or dichloromethane containing aluminum chloride. Oxidation of the methyl group of Formula XXXII affords the corresponding carboxylic acids, Formula XXXIII. Preferred oxidation conditions include high pressure reaction of oxygen gas in the presence of cobalt (II) acetate, using hydrogen bromide/acetic acid/methylethylketone/butane as solvent. Compounds are typically purified by chromatography on silica gel.

Additional methods for preparing the compounds of this invention will be apparent to those skilled in the art. For example, compounds of Formula XV where $R_4$ is hydrogen or lower alkyl can be converted to homologous compounds of the invention (Formula XV, where $R_4$ is higher alkyl) by methods employing Wittig reactions, Cadogan, J. I. G., ed., *Organophosphorus Reagents in Organic Synthesis*, Academic Press (London, 1979), aldol condensations, Nielson, *Organic Reactions*, 1–444 (1968); Mukaiyama, T., *Organic Reactions*, 28, Grignard reactions, and the like.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples temperatures are given in degrees celcius (°C.) and the quantities of materials in grams and milliliters unless otherwise noted.

DESCRIPTION OF THE PREFERRED EMBODIMENTS

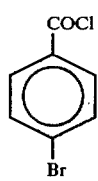

EXAMPLE 1

4-Bromobenzoyl Chloride

A solution of 4-bromobenzoic acid (0.113 moles) and thionyl chloride (45 ml) in carbon tetrachloride (100 ml) was heated at reflux for 3.5 hours. Solvent and excess thionyl chloride were removed under reduced pressure and the crude 4-bromobenzoyl chloride was used in subsequent reactions without further purification.

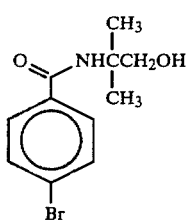

EXAMPLE 2

N-(1,1-dimethyl-2-hydroxyethyl)-4-bromobenzamide

To a cold solution (5° C.) of crude 4-bromobenzoyl chloride (0.11 moles) in methylene chloride (200 ml) was added dropwise over 1.5 hours a solution of 2-amino-2-methylpropanol (0.22 moles) in methylene chloride (50 ml) over 1.5 hours. After stirring for 72 hours at room temperature, the reaction was poured into water (200 ml). The layers were separated and the aqueous layer was washed with methylene chloride. The combined methylene chloride was washed with water, dried over sodium sulfate, filtered, and the solvent removed by a nitrogen stream to yield 27 g of a white solid. The title compound, having an nmr spectrum consistent with the assigned structure, was used without further purification in subsequent reactions.

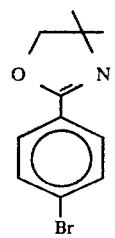

EXAMPLE 3

2-(4-bromophenyl)-4,5-dihydro-4,4-dimethyloxazole

To the title compound of Example 2 (0.1 moles) was added dropwise, in the cold, thionyl chloride (0.4 moles) over 35 min. After stirring for one hour, the reaction was transferred to an addition funnel and added dropwise to rapidly stirring diethyl ether (700 ml). After stirring for 20 hours, the white solid was filtered under reduced pressure and washed well with diethyl ether. The dry solid was treated with 20% sodium hydroxide (75 ml). After stirring for 30 minutes the product was extracted into diethyl ether, and the aqueous layer was washed with ether. The combined ether extracts were washed with water, dried over sodium sulfate, filtered and concentrated under reduced pressure to an oil. The oil was distilled under vacuum to yield 20.0 g of the title compound as a colorless liquid, b.p. 69°–73° C./0.04 mm Hg.

Analysis calcd. for $C_{11}H_{12}BrNO$: C, 51.99; H, 4.76; N, 5.51; Br, 31.44. Found: C, 51.53; H, 4.75; N, 5.34; Br, 31.57.

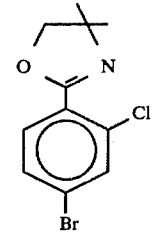

EXAMPLE 4

2-(2-chloro-4-bromophenyl)-4,5-dihydro-4,4-dimethyloxazole

The title compound was prepared according to the methods of Examples 1, 2, and 3. Structure assignment was supported by nmr, infrared, and ultraviolet spectra and by elemental analysis.

Analysis Calcd. for $C_{11}H_{11}NOClBr(288.57)$: C, 45.78; H, 3.84; N, 4.85. Found: C, 45.86; H, 3.93; N, 4.93.

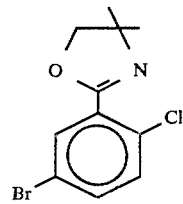

EXAMPLE 5

2-(2-chloro-5-bromophenyl)-4,5-dihydro-4,4-dimethyloxazole

The title compound was prepared according to the method of Example 4. Structure assignment was supported by the nmr spectrum and by elemental analysis.

Analysis calcd. for $C_{11}H_{11}NOClBr$ (288.57): C, 45.78; H, 3.84; N, 4.85; Cl, 12.29; Br, 27.69. Found: C, 45.97; H, 3.84; N, 4.85; Cl, 12.12; Br, 27.82.

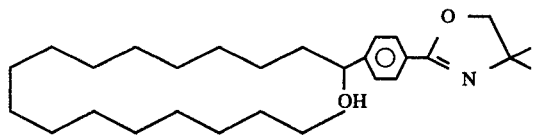

EXAMPLE 6

1-[4-(4,5-dihydro-4,4-dimethyl-2-oxazolyl)phenyl]-1-octadecanol

While under an argon atmosphere, a solution of the product of Example 3 (4 mmole) in tetrahydrofuran (100 ml) was cooled with stirring to ca. −75° C. n-Butyllithium (2 ml; 2.04M in hexane) was added dropwise using a syringe over 15 min. After stirring for 2 hours a second solution of octadecyl aldehyde (4 mmole) in tetrahydrofuran (100 ml) precooled to −5° C. was canulated to the above solution over 25 min., maintaining the temperature below −60° C. The reaction was allowed to warm to room temperature over the next 2.5 hours, then was quenched with water (10 ml) and stirred for 60 hours. Most of the tetrahydrafuran was evaporated under a stream of nitrogen. More water (100 ml) was added and the mixture was extracted into ethyl acetate. The combined extracts were dried over sodium sulfate and filtered, then the solvent was removed by a nitrogen stream to give an oil. The product was purified by chromatography on silica gel to give 0.80 g of the title compound, m.p. ca. 72°-75° C.

Analysis calcd. for $C_{29}H_{44}NO_2$(443.7): C, 78.50; H, 11.11; N, 3.16. Found C, 78.47; H, 11.17; N, 2.98.

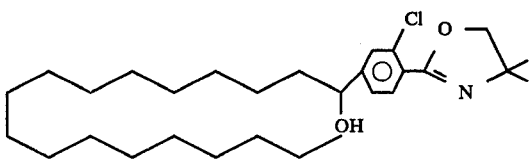

EXAMPLE 7

1-[3-chloro-4-(4,5-dihydro-4,4-dimethyl-2-oxazolyl)-phenyl]-1-octadecanol

A solution of the product of Example 4 (4 mmoles) in tetrahydrofuran (150 ml) was cooled to ca. −75° C. under an atmosphere of argon. n-Butyllithium (2 ml, 2.04M in hexane) was added by syringe over 15 min. while maintaining the reaction temperature below −70° C., and the solution then stirred for 3.5 hours. A cold solution (ca. −8° C.) of octadecyl aldehyde (4 mmoles) in tetrahydrofuran (100 ml) was canulated by syringe to the above solution over 25 min., keeping the temperature below −60° C. The reaction temperature rose to 25° C. during the next 2 hours, after which the reaction was quenched with water (10 ml) and stirred overnight. After removing the tetrahydrofuran under a nitrogen stream, water (75 ml) was added and the product extracted into ethyl acetate. The combined extract was dried over sodium sulfate, filtered and stripped under reduced pressure to give 1.7 g of an oil. The product was purified by chromatography on silica gel to give 0.85 g of the title compound, m.p. ca. 74°-78° C.

Analysis calcd. for $C_{29}H_{49}ClNO_2$ (478.2): C, 72.85; H, 10.12; N, 2.93; Cl, 7.41 Found C, 73.03; H, 10.30; N, 2.77; Cl, 7.33

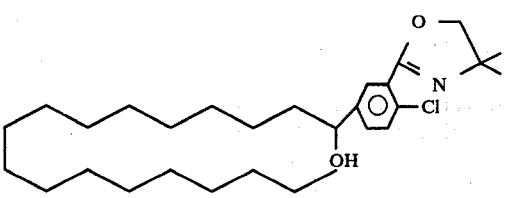

EXAMPLE 8

1-[4-chloro-3-(4,5-dihydro-4,4-dimethyl-2-oxazolyl)-phenyl]-1-octadecanol, Method A While under an argon atmosphere a solution of the title compound of Example 5 (0.016 moles) in tetrahydrafuran (400 ml) was cooled with stirring to ca. −75° C. n-Butyllithium (8 ml, 2.04M in hexane) was added by syringe over 35 min., maintaining a temperature below −72° C. The solution was then warmed to −55° C. and held at that temperature for 30 min. A solution of octadecyl aldehyde (0.016 moles) in tetrahydrafuran (75 ml) precooled to −2° C. was canulated to the above solution over 30 min., while maintaining the temperature below −50° C. The temperature was allowed to rise to −40° C. during 1 hour and held there 1.5 hours. The mixture was then cooled to ca. −75° C. and stirred overnight. The reaction was allowed to warm to 10° C. and then quenched with water (40 ml). The reaction was stirred for 2.5 hours, then the tetrahydrofuran was removed using a nitrogen stream. Water (150 ml) was added and the product extracted into ethyl acetate. The combined extract was dried over sodium sulfate, filtered and stripped under reduced pressure to give 8 g of an oil. The product was purified by chromatography on silica gel to give 1.5 g solid of the title compound, m.p. ca. 63°-68° C.

Analysis Calcd. for $C_{29}H_{48}ClNO_2$ (478.16): C, 72.85; H, 10.12; N, 2.93; Cl, 7.41. Found C, 73.11; H, 10.24; N, 2.93; Cl, 7.48.

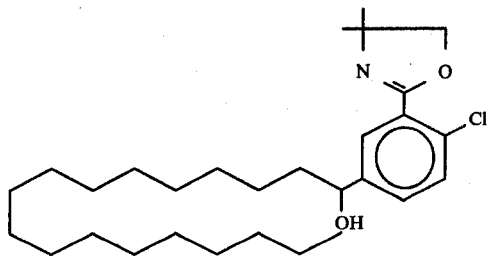

EXAMPLE 9

1-[4-3-(4,5-dihydro-4,4-dimethyl-2-oxazoly)phenyl]octadecanol, Method B

The reaction was carried out under an atmosphere of argon in dried glassware. The reaction vessel was charged with 0.24 g (0.01 mole) of magnesium metal and 25 ml of distilled tetrahydrofuran (THF), and the mixture was heated at reflux for one hour. The solvent was decanted, and 5 ml of fresh THF added. A portion of the title compound of Example 5 (2.9 gm) was added and the reaction was allowed to proceed. The remaining oxazoline was added, followed by an additional 15 ml of THF. The Grignard reagent was allowed to form over a period of 18 hours, or until all of the magnesium had reacted. Stearic aldehyde dissolved in 10 ml THF was added over a period of 20 minutes, and the reaction mixture was maintained at 0° for 2 hours. After being warmed to room temperature, the reaction mixture was poured into 250 ml of ice/conc. HCl mixture, and extracted several times with ether. The organic phase was dried over magnesium sulfate and concentrated, giving 3.97 g (83%) of crude product. The product was purified by chromatography, and recrystallized from methanol, giving 2.43 g (51%) of pure title product, identical with that prepared in Example 8.

Analysis. Calcd. for $C_{29}H_{48}ClNO_2$: C, 72.85; H, 10.12; N, 2.93; Cl, 7.41. Found: C, 72.92; H, 10.20; N, 2.63; Cl, 7.69.

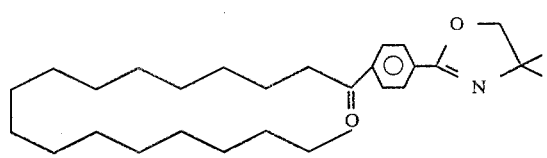

EXAMPLE 10

1-[4-(4,5-dihydro-4,4-dimethyl-2-oxazolyl)phenyl]-1-octadecanone

A mixture of the product of Example 6 (1.0 mmoles) and manganese dioxide (18.0 mmole) in methylene chloride (25 ml) was stirred at room temperature for 1 hour and then refluxed for 30 min. After cooling the mixture to room temperature, the insoluble material was suction filtered through a filtering aid and washed with methylene chloride. The combined filtrate and wash was concentrated under reduced pressure to an oil. The product was purified by chromatography on silica gel to give 330 mg of the title compound as a solid, m.p. ca. 73°–76° C.

Analysis Calcd. for $C_{29}H_{47}NO_2$ (441.7): C, 78.86; H, 10.72; N, 3.17. Found: C, 79.21; H 10.68; N, 3.49.

NMR (CDCl$_3$): methylene adjacent to new carbonyl, 3.0 ppm (t). Loss of C$\underline{H}$—OH at 4.7 ppm.

IR (CHCl$_3$): C=O, 1680 cm$^{-1}$; oxazoline, 1642 cm$^{-1}$ (No alcohol band).

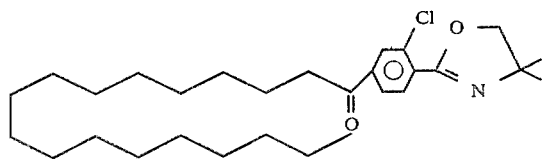

EXAMPLE 11

1-[3-chloro-4-(4,5-dihydro-4,4-dimethyl-2-oxazolyl)-phenyl]-1-octadecanone

The title compound, m.p. ca. 57°–60°, was prepared by the method of Example 10 using the product of Example 7 (1.6 mmoles) and manganese dioxide (17 mmoles) added in several portions.

Analysis calcd. for $C_{29}H_{46}ClNO_2$ (476.14): C, 73.14; H, 9.74; N, 2.94; Cl, 7.45. Found: C, 73.41; H, 9.79; N, 2.97; Cl, 7.21.

NMR (CDCl$_3$): methylene next to new carbonyl, 2.9 ppm (t)

IR (CHCl$_3$): C=O, 1690 cm$^{-1}$; oxazoline, 1650 cm$^{-1}$

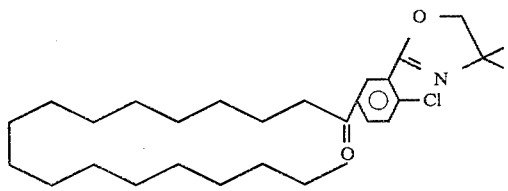

EXAMPLE 12

1-[4-chloro-3-(4,5-dihydro-4,4-dimethyl-2-oxazolyl)-phenyl]-1-octadecanone

The title compound was prepared by the method of Example 10 using the product of Example 8 (1.15 mmoles) and manganese dioxide (5.8 mmole) added in several portions.

Analysis calcd. for $C_{29}H_{46}ClNO_2$ (476.14): C, 73.15; H, 9.74; N, 2.94; Cl, 7.45. Found C, 73.28; H, 9.71; N, 3.21; Cl, 7.37.

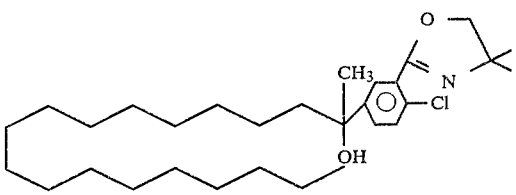

EXAMPLE 13

1-methyl-1-[4-chloro-3-(4,5-dihydro-4,4-dimethyl-2-oxazolyl)phenyl]octadecanol The title compound of Example 12 (11 mg) was dissolved in 2 ml of cold (ca. −78°) tetrahydrofuran to which was then added 0.5 ml of 3M methylmagnesium bromide, all under a dry argon atmosphere. After about ten minutes, the mixture was allowed to warm to room temperature and acidified with 1N hydrochloric acid. The mixture was extracted with ethyl acetate, and the organic phase was dried over sodium sulfate, filtered, and concentrated to dryness. Structure assignment was consistent with the nmr and ultraviolet spectra.

NMR (CDCl$_3$): methyl group, 1.5 ppm (s).
UV (MeOH): λmax 225 nm

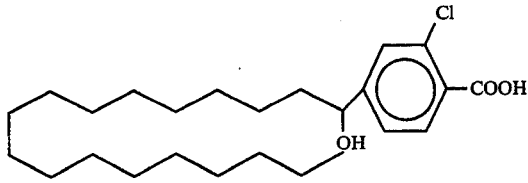

EXAMPLE 14

2-chloro-4-(1-hydroxyoctadecyl)benzoic acid

The product of Example 7 (1.0 mmoles) in 4.5N HCl (25 ml) was heated to 90° C. for 4 days. After cooling, the mixture was extracted with methylene chloride. The combined methylene chloride extracts were dried over sodium sulfate, filtered, and concentrated under reduced pressure to an oil. The product was purified by chromatography on silica gel, followed by recrystallization from methanol-hexane to yield 0.14 g of the title compound, m.p. ca. 93°–96° C.

Analysis calcd. for $C_{25}H_{41}ClO_3$ (425.03): C, 70.64; H, 9.72; Cl, 8.34. Found C, 70.53; H, 9.69; Cl, 8.45.

IR: C=O, 1700 cm$^{-1}$; —OH, 3610 cm$^{-1}$

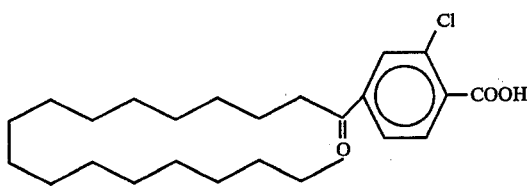

EXAMPLE 15

2-chloro-4-(1-oxooctadecyl)benzoic acid

The product of Example 11 (0.84 mmoles) in 4.5N HCl (7.5 ml) was heated at 70° C. for 5 days. After cooling the solution to room temperature, a white solid was filtered and washed with water (10 ml), then recrystallized from methanol-diethyl ether to yield 0.14 g of the title compound, m.p. ca. 96°–102° C.

Analysis calcd. for $C_{25}H_{39}ClO_3$ (423.0): C, 70.98; H, 9.29; Cl, 8.38. Found: C, 71.17; H, 9.44; Cl, 8.07.

IR (CHCl$_3$): C=O, 1690, 1735 cm$^{-1}$

UV: λmax 11,800

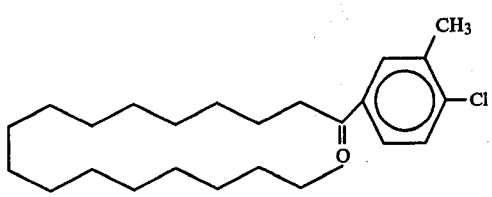

EXAMPLE 16

1-[(4-chloro-3-methyl)phenyl]-1-octadecanone 2-Chlorotoluene (5.7 ml, 6.27 g, 49.5 mmole) was dissolved in 20 ml of carbon disulfide (CS$_2$) followed by the addition of 7.92 g of aluminum chloride. Steroyl chloride (15 g) dissolved in 10 ml of CS$_2$ was then added in four portions. The reaction was stirred at room temperature for one hour, heated at reflux for 3 hours, then cooled to room temperature. The cooled reaction mixture was slowly decanted into an ice/1N HCl mixture with stirring. The organic solvents were allowed to evaporate overnight, and the organic residue removed. The aqueous phase was extracted once with benzene, and the organic phase combined with the organic residue. Concentration on a rotary evaporator gave a solid, which after air drying was recrystallized from methanol to give the title product, m.p. ca. 54° C.

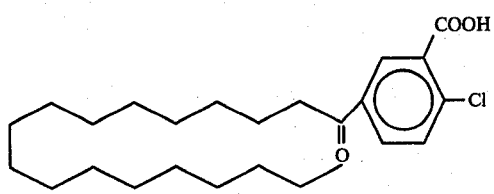

EXAMPLE 17

2-chloro-5-(1-oxooctadecyl)benzoic acid, Method A

The product of Example 16 (6.0 gm), 25 ml of glacial acetic acid 5 ml of hydrogen bromide in acetic acid 10 ml of methylethyl ketone and about 40 ml of n-butane were added to a stainless steel high-pressure bomb. After adding 0.5 g of cobalt(II) acetate tetrahydrate, the bomb was charged to about 200 psi with oxygen (O$_2$) gas. The bomb was heated to about 100° C. for about 6 hours. The oxygen was bled off and replaced with about 15 psi of nitrogen (N$_2$) gas and allowed to cool to room temperature. The contents of the bomb were added to water and filtered to give a wax. This material was dried and chromatographed on silica gel, eluting with increasing percentages of ethyl acetate in cyclohexane with about 1% of acetic acid added. The title compound was recrystallized from benzene/cyclohexane and characterized by mass spectrometry (M+/e=422 with the proper isotope ratio for one chlorine atom) and by elemental analysis.

Caldc. for $C_{25}H_{39}O_3Cl$: C, 70.98; H, 9.29. Found: C, 71.13; H, 9.30.

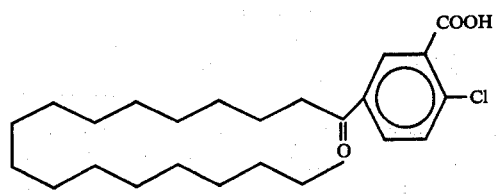

EXAMPLE 18

2-chloro-5-(1-oxooctadecyl)benzoic acid, Method B

The title compound was prepared by the method of Example 15 using 145 mg of the compound of Example 12. The compound thus formed was identical with that prepared by Example 17.

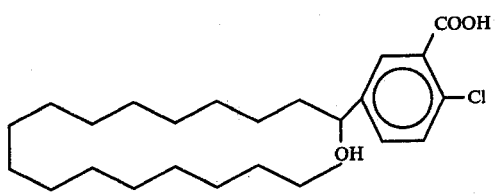

EXAMPLE 39

2-chloro-5-(1-hydroxyoctadecyl)benzoic acid

To a solution of the title compound of Example 17 (50 mg) in 5 ml of cold (ca. 0°) absolute ethanol was added in portions 25 mg of sodium borohydride. The mixture was allowed to warm to room temperature and stirred for four hours. A slight excess of 0.1N hydrochloric acid was added, and the resultant precipitate was collected, washed with water, and air-dried. Recrystallization from methanol gave the title compound, m.p. ca. 106°–107°.

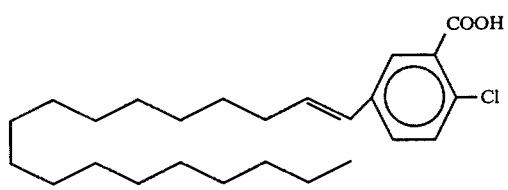

EXAMPLE 20

2-chloro-5-(1-octadecenyl)benzoic acid

The title compound was prepared from 360 mg of the title compound of Example 8 by the general method of Example 14, except that elimination was induced under refluxing conditions. Recrystallization from methanol afforded 262 mg of solid, m.p. ca. 79°–82°.

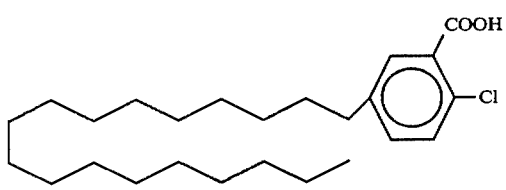

EXAMPLE 21

2-chloro-5-octadecylbenzoic acid

A solution of the title compound of Example 20 (25 mg) in ethanol is reduced with hydrogen gas at atmospheric pressure over Raney nickel catalyst. After hydrogen uptake ceases, the mixture is filtered and solvent removed under a nitrogen stream, giving the title compound.

CHART A

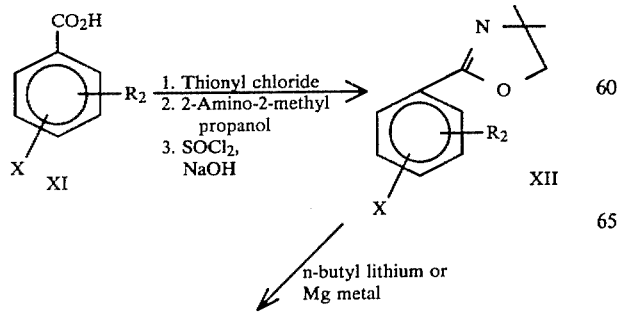

-continued
CHART A

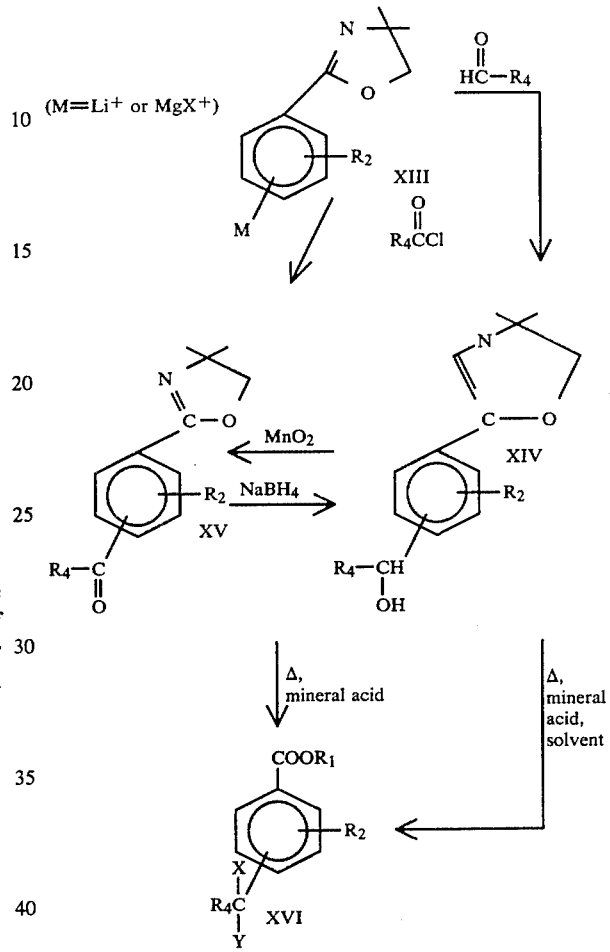

CHART B

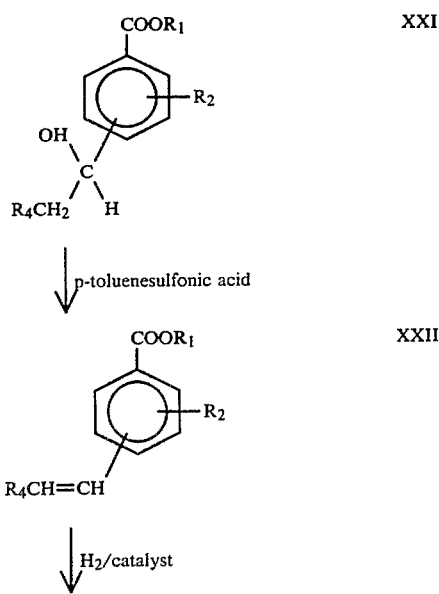

CHART B

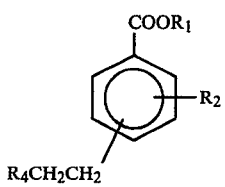   XXIII

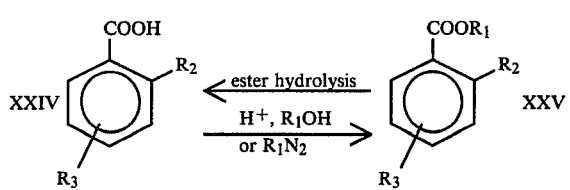

CHART C

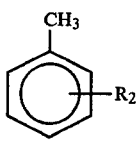

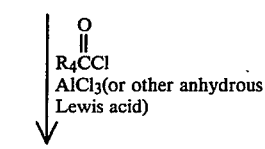   XXXI

|oxidation

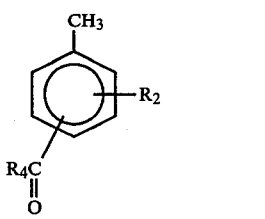   XXXII

-continued
CHART C

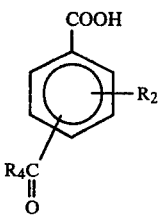   XXXIII

What I claim is:

1. A compound of the formula

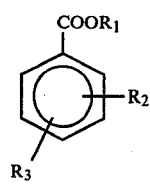

wherein $R_1$ is:
(a) hydrogen; or
(b) alkyl of 1 to 6 carbon atoms, inclusive
wherein $R_2$ is
(a) halogen; or
(b) trifluoromethyl;
wherein $R_3$ is:
(a) —C(O)$R_4$;
(b) —CH(OH)$R_4$;
(c) —CH$_2$$R_4$; or
(d) —CH=CH$R_4$;
wherein $R_4$ is alkyl of 13 to 25 carbon atoms inclusive and the pharmacologically acceptable base addition salts thereof.

2. A compound according to claim 1 wherein $R_3$ is —C(O)$R_4$.

3. 2-chloro-5-(1-oxooctadecyl)benzoic acid, a compound according to claim 2.

4. 2-chloro-4-(1-oxooctadecyl)benzoic acid, a compound according to claim 2.

5. A compound according to claim 1 wherein $R_3$ is —CH(OH)$R_4$.

6. 2-chloro-4-(1-hydroxyoctadecyl)benzoic acid, a compound according to claim 5.

7. 2-chloro-5-(1-hydroxyoctadecyl)benzoic acid, a compound according to claim 5.

8. A compound according to claim 1 wherein $R_3$ is —CH$_2$$R_4$.

9. 2-chloro-5-octadecyl benzoic acid, a compound according to claim 8.

10. A compound according to claim 1 wherein $R_3$ is —CH=CH$R_4$.

11. 2-chloro-5-(1-octadecenyl)benzoic acid, a compound according to claim 10.

* * * * *